US012013368B2

(12) United States Patent
Rajasekharan et al.

(10) Patent No.: US 12,013,368 B2
(45) Date of Patent: Jun. 18, 2024

(54) AQUEOUS SAMPLE MEASUREMENT VIA OXIDIZING METAL TO HIGHER VALENCE

(71) Applicant: HACH COMPANY, Loveland, CO (US)

(72) Inventors: Vishnu Rajasekharan, Fort Collins, CO (US); Russell Young, Fort Collins, CO (US); Richard Leggett, Dickinson, TX (US); Seamus O'Mahony, County Cork (IE)

(73) Assignee: HACH COMPANY, Loveland, CO (US)

( * ) Notice: Subject to any disclaimer, the term of this patent is extended or adjusted under 35 U.S.C. 154(b) by 757 days.

(21) Appl. No.: 17/253,474

(22) PCT Filed: Jul. 24, 2019

(86) PCT No.: PCT/US2019/043182
§ 371 (c)(1),
(2) Date: Dec. 17, 2020

(87) PCT Pub. No.: WO2020/023601
PCT Pub. Date: Jan. 30, 2020

(65) Prior Publication Data
US 2021/0116415 A1    Apr. 22, 2021

Related U.S. Application Data

(60) Provisional application No. 62/702,654, filed on Jul. 24, 2018.

(51) Int. Cl.
*G01N 27/416* (2006.01)
*G01N 21/80* (2006.01)
(Continued)

(52) U.S. Cl.
CPC ......... *G01N 27/4167* (2013.01); *G01N 21/80* (2013.01); *G01N 27/302* (2013.01);
(Continued)

(58) Field of Classification Search
None
See application file for complete search history.

(56) References Cited

U.S. PATENT DOCUMENTS

2005/0226774 A1    10/2005    Kounaves
2010/0089773 A1    4/2010    Kounaves
(Continued)

FOREIGN PATENT DOCUMENTS

| WO | 2010/080327 | 7/2010 | |
|---|---|---|---|
| WO | 2015061562 A1 | 4/2015 | |
| WO | WO-2017014695 A1 * | 1/2017 | ............ C02F 1/4672 |

OTHER PUBLICATIONS

International Searching Authority, Notification of Transmittal of the International Search Report and the Written Opinion of the International Searching Authority or the Declaration, dated Nov. 19, 2019, pp. 16.

*Primary Examiner* — J. Christopher Ball
(74) *Attorney, Agent, or Firm* — Ference & Associates LLC

(57) ABSTRACT

An embodiment provides a method for measuring at least one characteristic of an aqueous sample, including: introducing an aqueous sample into a measurement device comprising one or more electrodes; oxidizing a transition metal to produce a higher valent metal by applying an electrical potential between an anode and a cathode of the measurement device; oxidizing, using the higher valent metal as a catalyst, a material within the aqueous sample; measuring a characteristic of the aqueous sample based upon the oxidized material, using a measurement device selected from the group consisting of: an electrochemical measurement (Continued)

device and an optical measurement device; and optimizing the electrical potential and at least one reagent delivered to the measurement device based on the measurement of the characteristic. Other aspects are described and claimed.

17 Claims, 5 Drawing Sheets

(51) Int. Cl.
    *G01N 27/30*     (2006.01)
    *G01N 31/00*     (2006.01)
    *G01N 31/22*     (2006.01)
    *G01N 33/18*     (2006.01)

(52) U.S. Cl.
    CPC ......... *G01N 31/005* (2013.01); *G01N 31/221* (2013.01); *G01N 33/1846* (2013.01)

(56) References Cited

U.S. PATENT DOCUMENTS

| | | |
|---|---|---|
| 2015/0108009 A1 | 4/2015 | Rajasekharan et al. |
| 2015/0111304 A1 | 4/2015 | Leggett et al. |
| 2019/0033249 A1 | 1/2019 | O'Mahony et al. |

* cited by examiner

AQUEOUS SAMPLE MEASUREMENT VIA OXIDIZING METAL TO HIGHER VALENCE

CLAIM FOR PRIORITY

This application claims priority to U.S. Provisional Application No. 62/702,654 filed on Jul. 24, 2018, entitled "AQUEOUS SAMPLE MEASUREMENT", which is incorporated by reference herein in its entirety.

FIELD

This application relates generally to water quality measurement, and, more particularly, to measurement of a characteristic of aqueous sample by oxidizing materials within the aqueous sample using an oxidized higher valent metal.

BACKGROUND

Ensuring water quality is critical in a number of industries such as pharmaceuticals and other manufacturing fields. Additionally, ensuring water quality is critical to the health and well-being of humans, animals, and plants which are reliant on the water for survival. Two important parameters that are measured in water are total organic carbon (TOC) and/or chemical oxygen demand (COD). Measuring TOC and COD helps to determine the content of living organisms or decaying matter in the water sample. Measurement of TOC or COD may allow for identification of water quality to make sure that the water is suitable for drinking or for other sensitive uses.

BRIEF SUMMARY

In summary, one embodiment provides a method for measuring at least one characteristic of an aqueous sample, comprising: introducing an aqueous sample into a measurement device comprising one or more electrodes; oxidizing a transition metal to produce a higher valent metal by applying an electrical potential between an anode and a cathode of the measurement device; oxidizing, using the higher valent metal as a catalyst, a material within the aqueous sample; measuring a characteristic of the aqueous sample based upon the oxidized material, using a measurement device selected from the group consisting of: an electrochemical measurement device and an optical measurement device; and optimizing the electrical potential and at least one reagent delivered to the measurement device based on the measurement of the characteristic.

Another embodiment provides a measurement device for measuring at least one characteristic of an aqueous sample, comprising: at least one chamber; one or more series of electrodes at least partially disposed within one of the at least one chamber; a processor; and a memory device that stores instructions executable by the processor to: introduce an aqueous sample into a measurement device comprising one or more electrodes; oxidize a transition metal to produce a higher valent metal by applying an electrical potential between an anode and a cathode of the measurement device; oxidize, using the higher valent metal as a catalyst, a material within the aqueous sample; measure a characteristic of the aqueous sample based upon the oxidized material, using a measurement device selected from the group consisting of: an electrochemical measurement device and an optical measurement device; and optimizing the electrical potential and at least one reagent delivered to the measurement device based on the measurement of the characteristic.

A further embodiment provides a product for measuring at least one characteristic of an aqueous sample, comprising: a storage device having code stored therewith, the code being executable by the processor and comprising: code that introduces an aqueous sample into a measurement device comprising one or more electrodes; code that oxidizes a transition metal to produce a higher valent metal by applying an electrical potential between an anode and a cathode of the measurement device; code that oxidizes, using the higher valent metal as a catalyst, a material within the aqueous sample; code that measure a characteristic of the aqueous sample based upon the oxidized material, using a measurement device selected from the group consisting of: an electrochemical measurement device and an optical measurement device; and code that optimizes the electrical potential and at least one reagent delivered to the measurement device based on the measurement of the characteristic.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
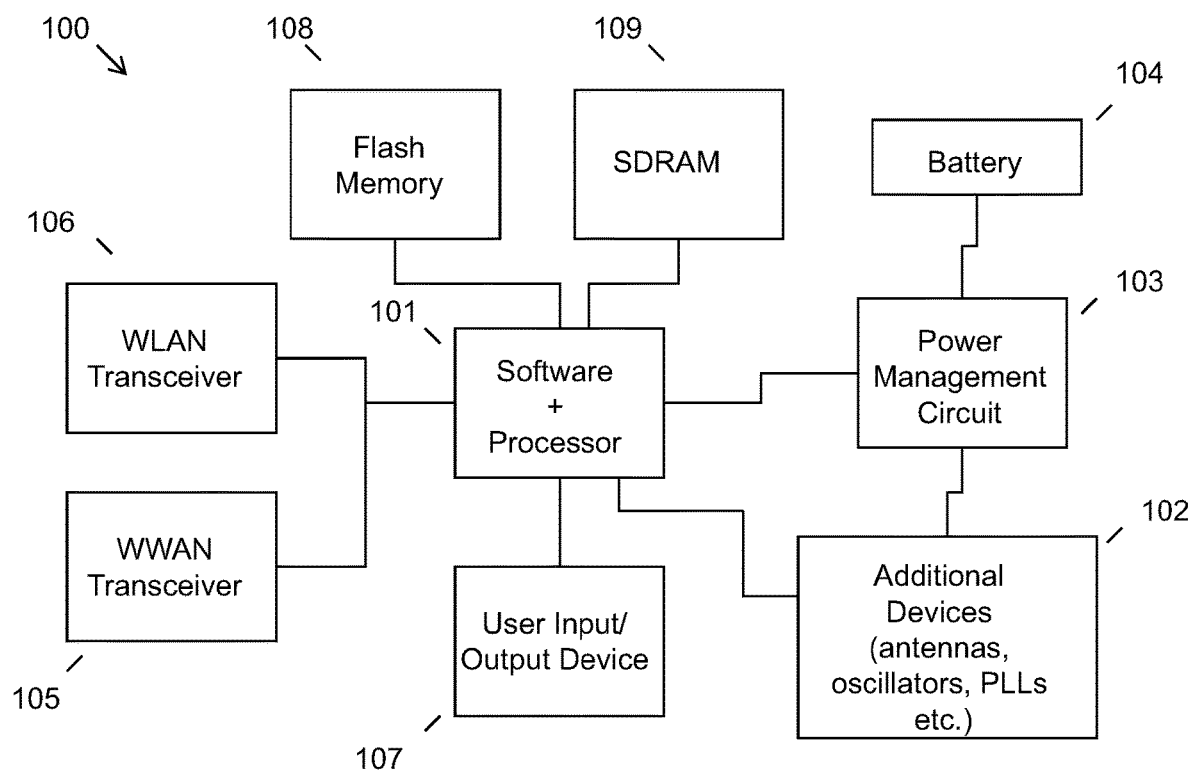
FIG. 1 illustrates an example of computer circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Ensuring water purity is critical in many applications, for example in municipalities that provide drinking water and in numerous other industries such as pharmaceuticals, chemicals and other manufacturing fields. The presence of organic compounds in the water may suggest a failure in filtration and/or other components and systems that, if left unchecked, can damage expensive industrial systems, impact product quality, be detrimental to public health, and even affect profit margins. As an example, drinking water quality will deteriorate if organics are present. Therefore, detecting the presence and concentration of organic contaminants in water samples is vital. Total organic carbon (TOC) analysis is the measurement of the level of organic molecules or contaminants in purified water and is often used as a non-specific indicator of water quality. Chemical oxygen demand (COD) tests may be a measure of the oxygen equivalent of the organic matter content of a sample susceptible to oxidation by the strong chemical oxidant. Thus, COD tests may use a strong chemical oxidant in an acid solution with heat to oxidize organic material to carbon dioxide, water, and other oxidation products.

Solid state reagent-less TOC or COD may utilize a thin diamond-film electrode doped with boron to carry out the oxidation of the organic material to produce carbon dioxide (e.g., by generating hydroxyl radicals and ozone on the surface of the boron doped diamond (BDD) electrode). The system can then measure the amount of carbon dioxide and correlate this measurement with a value or amount of organic compounds that are present in the aqueous sample. Previously available measurement devices may use boron doped diamond since it serves as a better electrode material than carbon-based or other metallic materials (e.g., silver, gold, mercury, nickel, etc.) because these materials poorly oxidize and may eventually themselves become oxidized.

The electrochemical measurement systems may use electrodes such as BDD electrodes to measure analytical parameters. Additionally or alternatively, the BDD electrodes may provide a means to perturb a system by providing electrical energy for oxidation of components of an aqueous sample. Systems focus on the use of a single source perturbation and detection. In other words, systems may use a separate component or system to perform the perturbation and detection functions. This single source approach limits the ability of a system to validate and gain confidence in a measurement. What is needed is a system that may measure analytical parameters of an aqueous sample and have the ability to perturb a system to improve accuracy and reduce complexity of the system, for example, by using more than one technique for perturbation and detection.

Accordingly, the systems and methods described herein provide a technique for measuring an analytical parameter of an aqueous sample and perturb a system. The system and method may be referred to as an in-situ spectroelectrochemical measurement. For example, the system may use an electrochemical technique to perturb the system and use an optical measurement technique. In an embodiment, an aqueous sample may be introduced into one or more chambers of the system. The system may have one or more electrodes. For example, the system may have a cathode and an anode. The cathode and the anode may be in the same chamber or compartment. One or more electrodes may be thick free standing solid BDD electrodes. Alternatively, the cathode and anode may be in separate chambers. In an embodiment, the two or more chambers may be separated by a membrane. The membrane may be electrically permeable, for example, the membrane may be Teflon® or a Teflon®-like material. TEFLON® is a registered trademark of The Chemours Company FC, LLC in the United States and other countries.

In an embodiment an electric signal (e.g., voltage, current, etc.) may be applied across a cathode and an anode of the measurement device, thereby applying an electrical signal to the aqueous solution. The electrical signal may oxidize a transition metal to produce a higher valent metal. This higher valent metal may have a measurable color. For example, the higher valent metal may be Fe(VI), Mn(VII), or other higher valent metal that may be visibly colored. The higher valent metal may be used as a catalyst to oxidize a material within the aqueous sample, for example, organic material, etc., thereby causing a change in the color of the higher valent metal. In an embodiment, a characteristic of the aqueous sample may be measured by measuring the colorimetric change in the higher valent metal. The amount of colorimetric change may be proportional to the amount of material within the aqueous sample. Thus, the system may use an electrochemical or optical measurement device to measure the characteristic of the aqueous sample. For example, in an embodiment, the carbon dioxide that is caused by oxidation of the organic material may be measured optically to determine TOC or COD. In an embodiment the optical measurement of the carbon dioxide may be performed using infrared measurement. In other words, species in an aqueous sample may be determined colorimetrically using visible spectroscopy or a spectrophometry instrument to determine the concentration of higher valent materials. In another example, in an embodiment, the pH of the incoming sample that is desired to be analyzed can be measured before, during, and after oxidation. The pH measurement can be enabled by a solid state SP2/SP3 carbon based electrode that is doped with boron. The electrode may be a SP3 substituted solid carbon electrode. These pH measurements will provide information to optimize the electrochemical perturbation and the consumption of reagents.

The illustrated example embodiments will be best understood by reference to the figures. The following description is intended only by way of example, and simply illustrates certain example embodiments.

While various other circuits, circuitry or components may be utilized in information handling devices, with regard to an instrument for testing a characteristic of an aqueous sample according to any one of the various embodiments described herein, an example is illustrated in FIG. 1. Device circuitry 100 may include a measurement system on a chip design found, for example, a particular computing platform (e.g., mobile computing, desktop computing, etc.) Software and processor(s) are combined in a single chip 101. Processors comprise internal arithmetic units, registers, cache memory, busses, I/O ports, etc., as is well known in the art. Internal busses and the like depend on different vendors, but essentially all the peripheral devices (102) may attach to a single chip 101. The circuitry 100 combines the processor, memory control, and I/O controller hub all into a single chip 101. Also, systems 100 of this type do not typically use SATA or PCI or LPC. Common interfaces, for example, include SDIO and I2C.

There are power management chip(s) 103, e.g., a battery management unit, BMU, which manage power as supplied, for example, via a rechargeable battery 104, which may be recharged by a connection to a power source (not shown). In at least one design, a single chip, such as 101, is used to supply BIOS like functionality and DRAM memory.

System 100 typically includes one or more of a WWAN transceiver 105 and a WLAN transceiver 106 for connecting to various networks, such as telecommunications networks and wireless Internet devices, e.g., access points. Additionally, devices 102 are commonly included, e.g., a transmit and receive antenna, oscillators, PLLs, etc. System 100 includes input/output devices 107 for data input and display/rendering (e.g., a computing location located away from the single beam system that is easily accessible by a user). System 100 also typically includes various memory devices, for example flash memory 108 and SDRAM 109.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform TOC or COD measurement of an aqueous sample.

Figure 2:
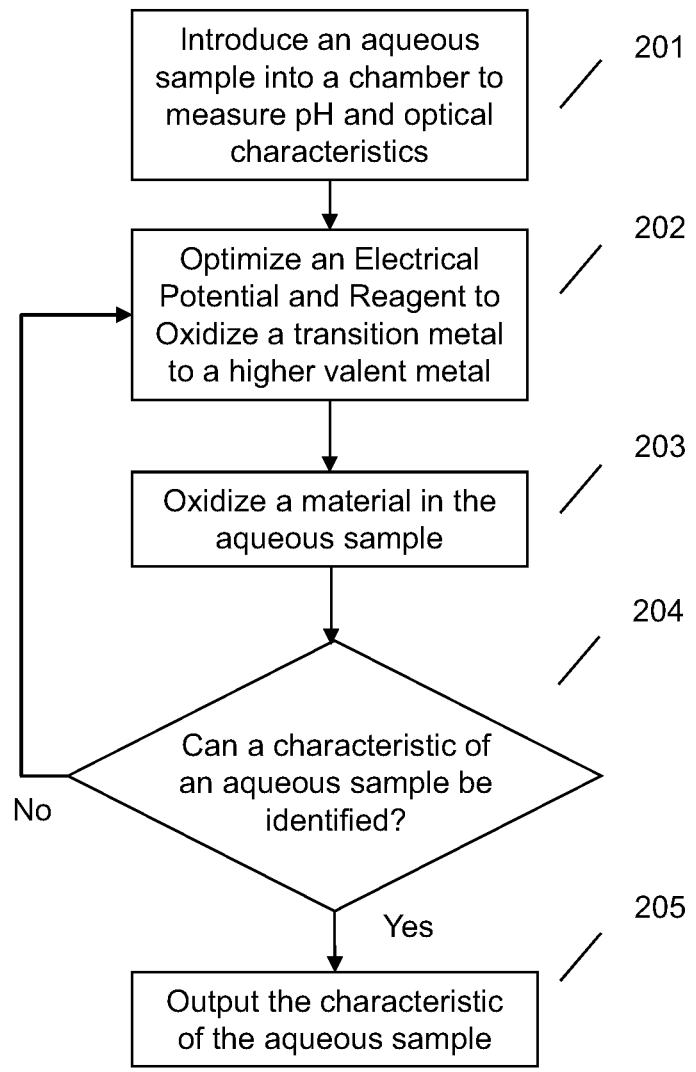
FIG. 2 illustrates a method of measuring a characteristic of an aqueous sample.

Referring now to FIG. 2, in an embodiment a system and method for measuring at least one characteristic of an aqueous sample. At 201, an aqueous sample may be introduced into a chamber of a measurement device. The aqueous sample may be placed or introduced into a test chamber manually by a user or using a mechanical means, for example, gravity flow, a pump, pressure, fluid flow, or the like. For example, a water sample for TOC or COD testing may be introduced to a chamber by a pump. In an embodiment, there may be one or more chambers in which the one or more method steps may be performed. In an embodiment, valves or the like may control the influx and efflux of the aqueous solution into or out of the one or more chambers, if present. Once the sample is introduced to the measurement system, the system may measure the TOC or COD content of the sample.

At 202, the system may oxidize a transition metal to produce a higher valent metal by applying an electrical potential to the aqueous sample in a test chamber. The electrical potential may be applied to one or more electrodes of the measurement device. In an embodiment, the electrodes may be fully or at least partially disposed in the volume of aqueous solution. For example, if the aqueous solution is introduced into a chamber having one or more electrodes, the aqueous solution may at least partially cover the one or more electrodes. As another example, the one or more electrodes may be partially disposed within the chamber with the other portion of the electrode outside the chamber. Thus, when the aqueous solution is introduced into the chamber it only covers the portion of the electrodes that are within the chamber.

In an embodiment, the electrical signal may be controlled using circuitry illustrated in FIG. 1. In an embodiment, the electrical signal may be a steady signal, a ramp, a pulse, or the like. The electrical signal may be applied until a threshold is reached. The threshold may be predetermined or a parameter/output may be recorded in real-time and adjust the electrical signal. An electrical signal may be altered based on reaction parameters such as components of the aqueous sample, condition of one or more electrodes, or the like.

Figure 3:
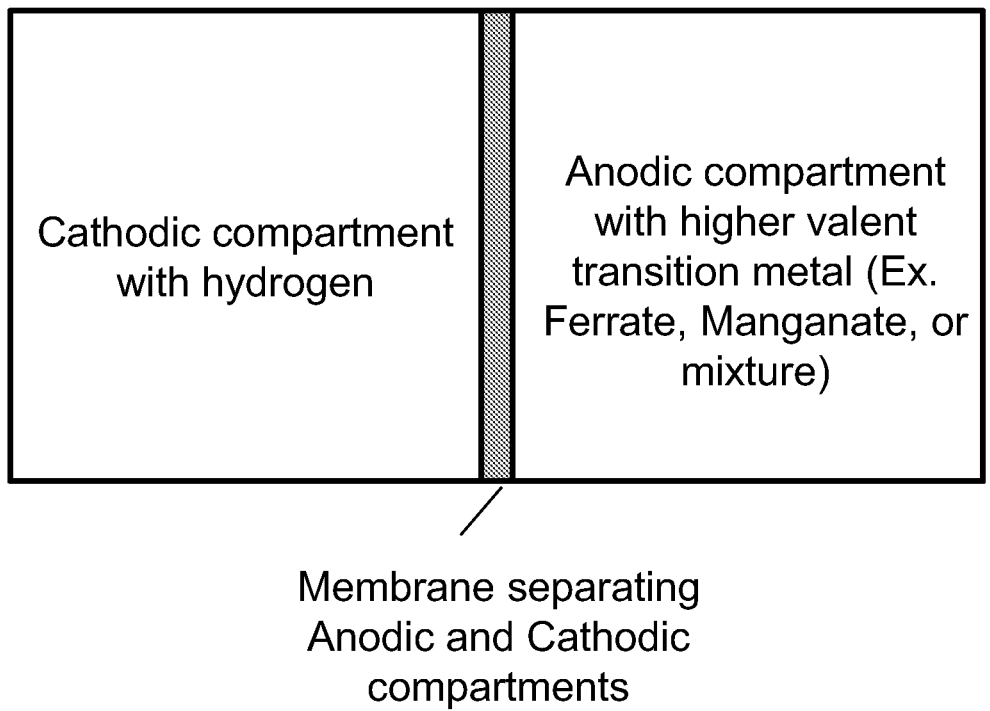
FIG. 3 illustrates a schematic of cathodic and anodic compartments in an example embodiment.

In an embodiment, the electrodes may include an anode and a cathode of the measurement device. Thus, the electrical signal may pass between the anode and cathode. Referring to FIG. 3, the aqueous sample may be in two chambers or compartments. For example, a first chamber may contain the cathode. The cathodic chamber may produce hydrogen. A second chamber may contain an anode. The anodic chamber may contain lower valent transition metals like iron and manganese initially and subsequently may produce ferrate and manganate. In an embodiment the cathodic chamber and the anodic chamber may be separated by a membrane. Thus, in an embodiment, the membrane may be made of a material that allows the electric signal to pass between the cathode and the anode, for example, a TEFLON® or TEFLON®-like material. In an embodiment, the membrane may increase the production of ferrate or manganate and/or allow a ferrate or manganate plume to concentrate in a chamber.

The electrical signal between a cathode and an anode may electrochemically oxidize a metal, for example, the electrical signal may cause a transition metal to oxidize to a higher valent metal, for example, due to an electrochemical reaction. As an example, the transition metal may include iron, manganese, nickel, chromium, or the like. In an embodiment, Fe and Mn may be fused together to produce an alloy. The alloy may enable production of a higher valent species. These transition metals may oxidize to higher valent metals, for example, Fe(VI) in the case of an iron transition metal, Mn(VII) in the case of a manganese transition metal, and the like. In the case that an alloy is used as a transition metal, for example, an iron/manganese alloy, the higher valent iron and manganese species would provide a ratiometric determination of the higher valent iron and manganese species that may eliminate the need for a reference peak, thereby resulting in a calibration-less system. Each of the manganese species exhibit different color. The existence of these different species is dependent on the pH of the solution. The color may be used to estimate the pH of the solution. Transition metals like iron and manganese when oxidized by stable electrodes may form higher valent species like Iron (V), Iron (VI), and/or Mn(VII). Their absorption spectra along with an increase or decrease in the absorption intensity may be used to optimize the system performance by varying applied power & electrode distance. The end point of oxidation may also be estimated by this measurement. This is a diagnostic capability that may be present in these systems.

An oxidation state or oxidation number may indicate a degree of oxidation. Oxidation is the loss of electrons in a chemical compound. An oxidation state, which may be a positive, negative, or zero value, may represent a charge an atom would have if all bonds were ionic with no covalent component. The transition metal may be on a boron doped diamond (BDD) substrate. Thus, using the example of the transition metal iron, the transition metal and BDD electrode in combination with an electrical signal may produce a thick plume of ferrate or manganate. A plume of ferrate may be produced at the anode, for example, in an anodic compartment. BDD is an intrinsically conductive or a semi-conductive substrate.

The higher valent metal may have a measurable color. In other words, while the transition metal itself may not have a color or be of a color that is not measurable, the higher valent metal may have a measurement color. Thus, the volume or amount of these higher valent metals may be measured, for example, using an infrared measurement device, spectrometer, colorimetric measurement device, or other optical measurement device. In other words, the higher valent metal species can be determined colorimetrically using visible spectroscopy to determine the concentration of the higher valent metals.

Determining the concentration of the higher valent metals not only allows for measurement of materials in the aqueous solution, as described in more detail below, but also allows the power delivered to the system to be optimized. Additionally, the spectroelectrochemical feedback would provide a means to optimize the efficiency of the system and also provide validation of the oxidation capacity of the system. As one example, this feedback would allow optimization of the cell volume. Parameters of the system may be adjusted based upon these findings. For example, the volume of one or more chambers of the system may be changed. A volume may be changed by physically altering the dimension of a chamber. This changing of volume may be accomplished by swapping out a chamber, or by altering the volume of a chamber with a plunger type arrangement. Additionally or alternatively, the volume of aqueous sample may be altered.

Figure 4:
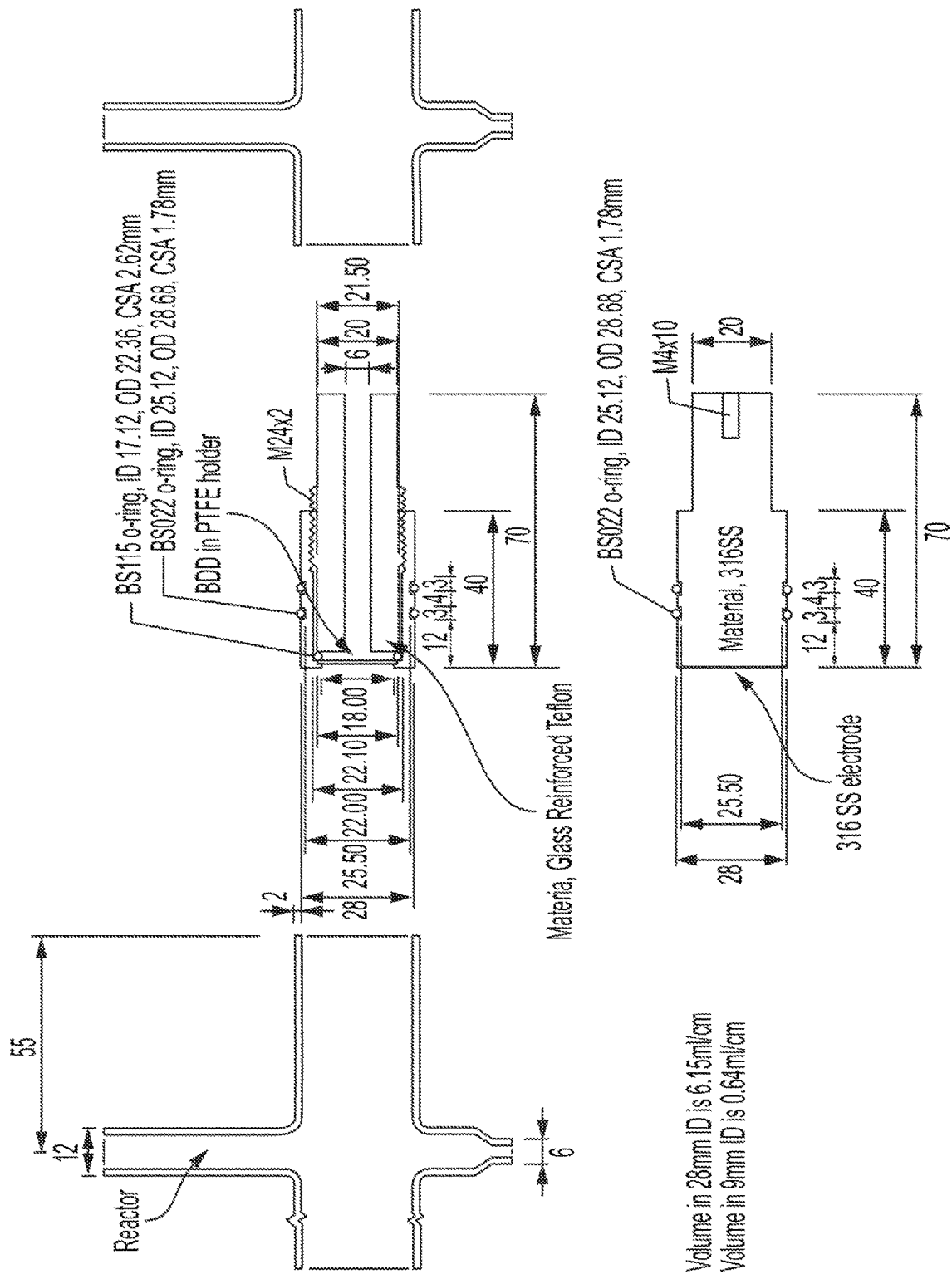
FIG. 4 illustrates an example device for measuring a characteristic of an aqueous sample.

As another example, this feedback would allow optimization of the distance between electrodes. Referring to FIG. 4, a cathode and an anode may be inserted into opposite ends of the lumen of a tube. In an embodiment, a cathode and/or anode may be moved closer together or farther apart. A distance between the electrodes may be optimized by successive reactions and preselected for a given reaction measurement. Additionally, or alternatively, a distance between electrodes may be altered in real time. A movement or changing a distance between electrode may also alter a volume of a chamber. In an embodiment, a cathode and an anode may move independently of one another.

As an additional example, this feedback would allow optimization of the concentration of transition metal species. The oxidation of a transition metal may serve to catalyze the oxidation of organics in the aqueous sample. Therefore, altering the concentration of transition metals may alter the kinetics of the system. For example, if an aqueous sample with higher concentration of organics is being measured, a higher concentration of transition metals may be required to provide a proper catalyst component to the system.

In a further example, this feedback would allow optimization of the amount of sparging to quantify carbon dioxide from the oxidation of organics in an aqueous sample. Sparging usually involves bubbling a chemically inert gas through a liquid. The sparging technique may be used to remove dissolved gas or gases from a liquid. In an embodiment, the pressure or partial pressure of the system may be altered. Additionally or alternatively, an amount of cavitation due to bubble formation may be altered or perturbed.

As final example, the feedback would allow optimization of the electrical signal applied to the system to optimize the reaction. The electrical signal may be an applied voltage. For example, an aqueous sample to be tested may be introduced to a chamber containing one or more series of electrodes. In an embodiment, the electrical signal applied to the electrodes, and thereby to the aqueous solution, may be a voltage signal. The system may also use a combination of electrical signals, for example, by initially applying a current and then applying a voltage. The system can then measure the electrical response (e.g., current value, voltage value, etc.) that results from the application of the electrical signal to the aqueous solution.

The applied electrical signal may be any electrical signal selected from a waveform group, for example, a pulse, a step, a ramp, a sawtooth, a sine wave, a square, a triangle, a continuous signal, or the like or any combination thereof. Thus, the applied electrical signal may be applied as a constant signal or may be applied as pulses or intermittent electrical signals. In an embodiment, the amplitude may be the same or variable. For example, a first amplitude may be applied and then a second amplitude may be applied. In an embodiment, the period may be the same or variable. The electrical signal may be a preprogrammed waveform, may be altered during a measurement, and/or may be controlled by the system or by a user.

Circuitry may control the electrical signal (e.g., current, voltage, etc.) to one or more series of electrodes such that different electrical signals may be applied to the volume of aqueous solution. In the case that multiple or a series of electrodes are included in the system, each electrode may correspond to a different electrical signal value. For example, a first electrode may correspond to a first electrical signal value, a second electrode may correspond to a second electrical signal value, and the like. Thus, as the system provides electrical signals to each of the electrodes, different components of the aqueous sample may be oxidized. In the case that a single electrode is used, the system may apply different electrical signals to the single electrode, each with an increasing electrical signal value. In either case, after each application of an electrical signal, the system may measure the TOC or COD of the aqueous solution.

At 203, the higher valent metal may be used as a catalyst to oxidize a material within the aqueous sample. For example, the higher valent material may be used as a catalyst to oxidize organic material in the aqueous sample. The use of a higher valent material to catalyze oxidation or organic material is described in U.S. Pat. No. 9,476,866, which is incorporated by reference in its entirety herein. Using optical perturbation like ultraviolet (UV) or visible light on the BDD substrate, for example, a thick-free standing solid BDD substrate, enables photochemical processes that can induce oxidation or reduction reactions. As a specific example, in the case of oxidizing organic materials, a UV light may be shone on the BDD semiconducting electrode while an electrochemical reduction potential is applied to the BDD. This causes the carbon dioxide produced by the organic material to be reduced to carbon monoxide, which can then be used to quantify the amount of carbon dioxide present in the system.

Figure 5:
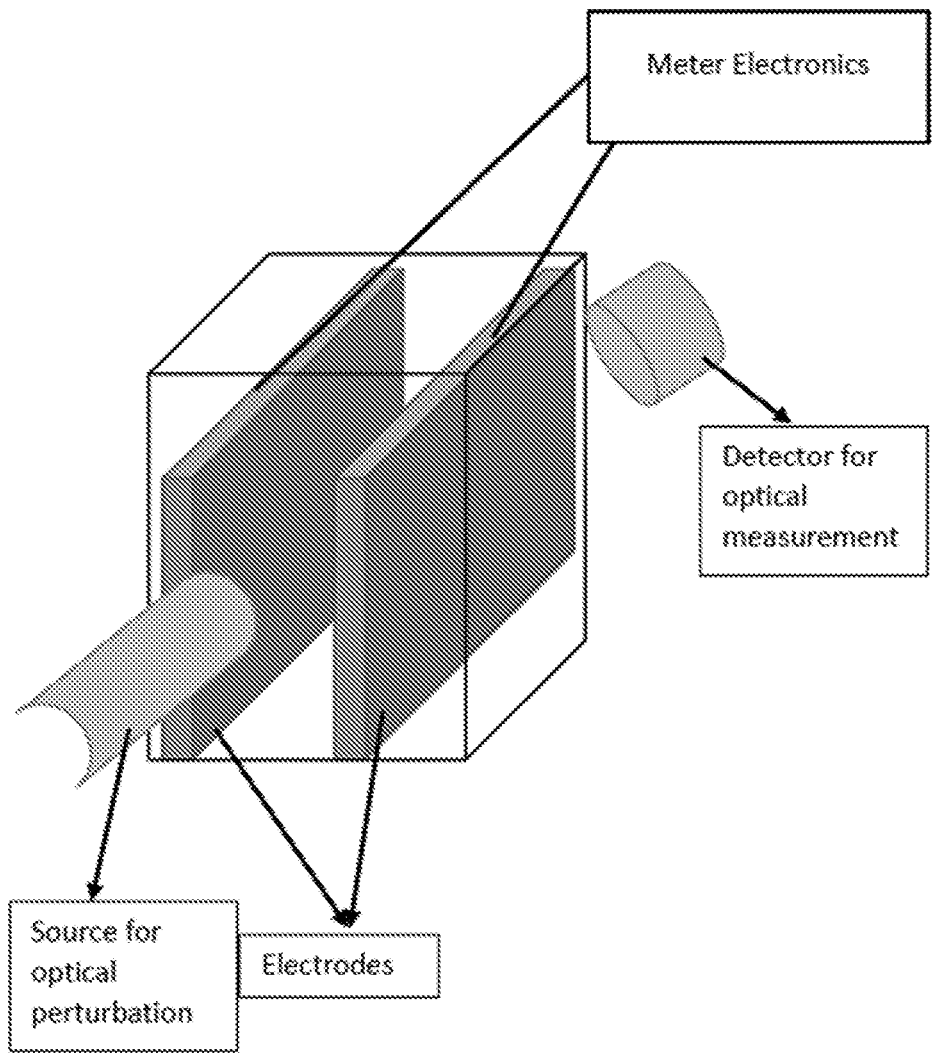
FIG. 5 illustrates another example device for measuring a characteristic of an aqueous sample.

In an embodiment, the system may use ultraviolet light for optical perturbation (See FIG. 5). Ultraviolet light may cost less or require less space and complexity to a system as compared to infrared light. Carbon dioxide generated from the electrochemical oxidation may be photoelectrochemically detected by a semiconducting BDD electrode. The amount of dopant boron can be controlled during the manufacture of BDD electrode to enable it to be used as a semiconducting substrate. Thus, the degree of semiconducting property can be tuned by adjusting the amount of boron that is incorporate into the diamond substrate. This feature can be used to tune the band-gap of the semiconducting boron doped substrate.

In an embodiment, other metal particles may be introduced. For example, modifications of metal nanoparticle such as silver may accelerate the reduction of carbon dioxide to carbon monoxide. This reduction may be quantified by measurement of electrochemical currents.

At 204, the system may determine whether a characteristic of an aqueous sample can be identified or measured.

Example characteristics that can be measured include pH, absorbance wavelength (color), total organic carbon (TOC), and the like. To measure the characteristic the system may employ a measurement device, for example, an electrochemical measurement device, an optical measurement device, or the like. In an embodiment, the characteristic may include the amount of organics in the aqueous sample. Since the organics are oxidized using the higher valent metal, the carbon dioxide may be measured electrochemically by meter electronics to determine TOC or COD (see FIG. 5). In an embodiment, the carbon dioxide may be measured optically to determine TOC or COD (see FIG. 5). For example, since the higher valent metal is of a measurable color, as the metal is used as a catalyst to oxidize the material in the aqueous sample, the higher valent metal is used, thereby causing a colorimetric change. This colorimetric change can be measured using different measurement devices. For example, the optical measurement may be performed using infrared measurement. In an embodiment, the Fe(VI), Mn(VII), and other transition metals may be visibly colored. For example, species in an aqueous sample may be determined colorimetrically using visible spectroscopy to determine the concentration of higher valent materials. For example, $Mn^{2+}$ may be a pale pink, $Mn(OH)_3$ containing Mn(III) as dark brown, $MnO_2$ containing Mn(IV) as black, Mn(VI) containing $(MnO_4)_2^-$ as green, Mn(VII) containing $MnO_4^-$ as purple, or the like. The resulting color from a reaction may be determined photometrically, for example, using a spectrophotometer. Alternatively or additionally, the resulting color from a reaction may be observed visually.

At 204, if a characteristic of an aqueous sample cannot be determined, the system may continue to apply an electrical potential at 202. In an embodiment, the system may apply the same electrical potential as previously applied or may alter the electrical potential to a different amplitude, waveform, or the like. Additionally, the system may alter parameters as outlined above to optimize the system. The optimizations may include changes to an electrical potential, altering a distance between a cathode and an anode, altering the volume of a chamber, altering a volume of the aqueous sample, altering the concentration of the transition metal, or the like.

If, however, at 204, if a characteristic of an aqueous sample may be determined, the system may output the characteristic of an aqueous solution. An output may be in the form of a display, storing the data to a memory device, sending the output through a connected or wireless system, printing the output, or the like. The system may be automated. The system may have associated alarms, limits, or predetermined thresholds. For example, if a measured characteristic reaches a threshold, the system may trigger an alarm, adjust the characteristic of the aqueous solution, alter the flow of the aqueous solution, or the like. Data may be analyzed in real-time, stored for later use, or any combination thereof.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device such as illustrated in FIG. 1, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring at least one characteristic of an aqueous sample, comprising:
   introducing an aqueous sample with a transition metal into a measurement device comprising one or more electrodes, wherein the measurement device comprises a membrane disposed between an anode and a cathode, and wherein the position of the membrane can be adjusted between the anode and the cathode;
   oxidizing a transition metal to produce a higher valent metal by applying an electrical potential between the anode and the cathode of the measurement device;
   oxidizing, using the higher valent metal as a catalyst, a material within the aqueous sample;
   measuring a characteristic of the aqueous sample based upon the oxidized material, using a measurement device selected from the group consisting of: an electrochemical measurement device and an optical measurement device; and optimizing the electrical potential and at least one reagent delivered to the measurement device based on the measurement of the characteristic.

2. The method of claim 1, wherein the higher valent metal comprises a metal having a measurable color.

3. The method of claim 2, wherein the oxidizing a material within the aqueous sample causes a measurable colorimetric change in the color of the higher valent metal.

4. The method of claim 3, wherein the measuring a characteristic of the aqueous sample comprises measuring the colorimetric change.

5. The method of claim 1, wherein a distance between the anode and the cathode is adjustable.

6. The method of claim 1, wherein at least one of the anode or the cathode comprises a SP3 substituted solid carbon electrode material.

7. The method of claim 1, wherein the measuring a characteristic comprises measuring total organic carbon.

8. The method of claim 1, wherein the oxidizing a material comprises using ultraviolet perturbation.

9. The method of claim 1, wherein the measuring comprises using at least one of: a colorimetric detection and a pH determination.

10. A measurement device for measuring at least one characteristic of an aqueous sample, comprising:

at least one chamber;

one or more series of electrodes at least partially disposed within one of the at least one chamber;

a processor; and a memory device that stores instructions executable by the processor to:

introduce an aqueous sample with a transition metal into a measurement device comprising one or more electrodes, wherein the measurement device comprises a membrane disposed between an anode and a cathode, and wherein the position of the membrane can be adjusted between the anode and the cathode;

oxidize a transition metal to produce a higher valent metal by applying an electrical potential between the anode and the cathode of the measurement device;

oxidize, using the higher valent metal as a catalyst, a material within the aqueous sample;

measure a characteristic of the aqueous sample based upon the oxidized material, using a measurement device selected from the group consisting of: an electrochemical measurement device and an optical measurement device; and optimizing the electrical potential and at least one reagent delivered to the measurement device based on the measurement of the characteristic.

11. The measurement device of claim 10, wherein the higher valent metal comprises a metal having a measurable color.

12. The measurement device of claim 11, wherein the oxidizing a material within the aqueous sample causes a measurable colorimetric change in the color of the higher valent metal.

13. The measurement device of claim 12, wherein the measuring a characteristic of the aqueous sample comprises measuring the colorimetric change.

14. The measurement device of claim 10, wherein a distance between the anode and the cathode is adjustable.

15. The measurement device of claim 10, wherein at least one of the anode or the cathode comprises a SP3 substituted solid carbon electrode material.

16. The measurement device of claim 10, wherein the measuring a characteristic comprises measuring at least one of: total organic carbon, absorbance wavelength, and pH.

17. The measurement device of claim 10, wherein the oxidizing a material comprises using ultraviolet perturbation.

* * * * *